(12) United States Patent
Panzenbeck et al.

(10) Patent No.: US 12,310,566 B2
(45) Date of Patent: May 27, 2025

(54) REAL-TIME SAMPLING SYSTEM

(71) Applicant: OLYMPUS MEDICAL SYSTEMS CORPORATION, Hachioji (JP)

(72) Inventors: Jason T. Panzenbeck, Seattle, WA (US); David A. Herrin, Seattle, WA (US); Christopher R. Ralph, Woodinville, WA (US)

(73) Assignee: Olympus Medical Systems Corporation, Tokyo (JP)

( * ) Notice: Subject to any disclaimer, the term of this patent is extended or adjusted under 35 U.S.C. 154(b) by 903 days.

(21) Appl. No.: 16/999,230

(22) Filed: Aug. 21, 2020

(65) Prior Publication Data

US 2021/0059648 A1    Mar. 4, 2021

Related U.S. Application Data

(60) Provisional application No. 62/923,262, filed on Oct. 18, 2019, provisional application No. 62/892,256, filed on Aug. 27, 2019.

(51) Int. Cl.
*A61B 10/04*    (2006.01)
*A61B 1/00*    (2006.01)
(Continued)

(52) U.S. Cl.
CPC .......... *A61B 10/04* (2013.01); *A61B 1/00066* (2013.01); *A61B 1/00098* (2013.01);
(Continued)

(58) Field of Classification Search
CPC . A61B 10/04; A61B 1/00066; A61B 1/00098; A61B 1/0011; A61B 1/00154;
(Continued)

(56) References Cited

U.S. PATENT DOCUMENTS

| 5,910,105 A | 6/1999 | Swain et al. |
| 2007/0021730 A1 | 1/2007 | Flaherty et al. |

(Continued)

FOREIGN PATENT DOCUMENTS

| CN | 107920811 | 4/2018 |
| CN | 112438685 | 3/2021 |

(Continued)

OTHER PUBLICATIONS

"United Kingdom Application Serial No. 2013287.4, Search Report mailed Jan. 29, 2021", 3 pgs.

(Continued)

*Primary Examiner* — Eric J Messersmith
*Assistant Examiner* — Kyle W. Kretzer
(74) *Attorney, Agent, or Firm* — Schwegman Lundberg & Woessner, P.A.

(57) ABSTRACT

A device and system for allowing real-time viewing of a procedure beyond a distal end of an endoscope. An exemplary device includes a sheath that has at least two lumens and a handle. The handle includes a connector that connects to a proximal end of an endoscope, a shaft portion that rotatably connects to a proximal end of the connector and a manifold that is slidably received by the shaft portion. The manifold connects to the sheath and allows for insertion of a radial ultrasound probe and a medical tool into the sheath. A stopping device in the manifold avoids accidental needle deployment.

17 Claims, 14 Drawing Sheets

(51) Int. Cl.
  *A61B 1/018* (2006.01)
  *A61B 8/00* (2006.01)
  *A61B 8/12* (2006.01)
  *A61B 10/00* (2006.01)
  *A61M 25/00* (2006.01)

(52) U.S. Cl.
  CPC ........ *A61B 1/0011* (2013.01); *A61B 1/00154* (2013.01); *A61B 1/018* (2013.01); *A61B 8/12* (2013.01); *A61B 8/445* (2013.01); *A61B 10/00* (2013.01); *A61B 2010/045* (2013.01); *A61M 2025/0059* (2013.01)

(58) Field of Classification Search
  CPC ........... A61B 1/018; A61B 8/12; A61B 8/445; A61B 2010/045; A61B 1/00133; A61B 8/0841; A61M 2025/0059
  See application file for complete search history.

(56) References Cited

U.S. PATENT DOCUMENTS

| | | | |
|---|---|---|---|
| 2010/0228084 A1* | 9/2010 | Sato ................... | A61B 1/00128 600/106 |
| 2012/0089022 A1* | 4/2012 | House ..................... | A61B 8/12 600/439 |
| 2013/0018359 A1 | 1/2013 | Coyle | |
| 2016/0128725 A1* | 5/2016 | Hatakeyama ...... | A61B 1/00137 606/185 |
| 2016/0331358 A1* | 11/2016 | Gordon ................. | A61B 10/04 |
| 2017/0055967 A1* | 3/2017 | Raybin ................... | A61B 8/12 |
| 2018/0279868 A1 | 10/2018 | Sczaniecka et al. | |
| 2020/0297311 A1 | 9/2020 | Baillargeon et al. | |
| 2020/0359995 A1* | 11/2020 | Walsh ................... | A61B 10/04 |

FOREIGN PATENT DOCUMENTS

| | | |
|---|---|---|
| DE | 102020121372 | 3/2021 |
| FR | 3100122 | 3/2021 |
| GB | 2589429 | 6/2021 |
| GB | 2589429 B | 5/2023 |
| GB | 2616981 | 9/2023 |
| JP | H11513577 | 11/1999 |
| JP | 2001037765 | 2/2001 |
| JP | 2001104315 A | 4/2001 |
| JP | 2010269126 | 12/2010 |
| JP | 2012008902 | 1/2012 |
| JP | 2017005596 | 1/2017 |
| JP | 2017504377 | 2/2017 |
| JP | 2018529403 | 10/2018 |
| JP | 2020029731 | 2/2020 |
| JP | 2020035999 | 3/2020 |
| JP | 2021030088 | 3/2021 |
| WO | 2015033618 | 3/2015 |
| WO | 2017040414 | 3/2017 |
| WO | 2020236598 | 11/2020 |

OTHER PUBLICATIONS

"France Application Serial No. 2008688, Office Action mailed Jan. 21, 2021", with machine translation, 4 pgs.

"France Application Serial No. 2008688, Response filed Mar. 21, 2021 to Office Action mailed Jan. 21, 2021", with machine translation, 4 pgs.

"United Kingdom Application Serial No. 2305262.4, Search Report mailed Jul. 24, 2023", 4 pgs.

"Japanese Application Serial No. 2020-142492, Notification of Reasons for Rejection mailed May 13, 2024", W English Translation, 11 pgs.

"Japanese Application Serial No. 2020-142492, Response filed Aug. 13, 2024 to Notification of Reasons for Rejection mailed May 13, 2024", W English Claims, 12 pgs.

"Japanese Application Serial No. 2020-142492, Final Notification of Reasons for Refusal mailed Sep. 9, 2024", w English translation, 6 pgs.

"Chinese Application Serial No. 202010760005.X, Office Action mailed Sep. 11, 2024", W English Translation, 26 pgs.

"Japanese Application Serial No. 2020-142492, Response filed Dec. 3, 2024 to Final Notification of Reasons for Refusal mailed Sep. 9, 2024", w english claims, 8 pgs.

"Chinese Application Serial No. 202010760005.X, Response filed Jan. 13, 2025 to Office Action mailed Sep. 11, 2024", W English Claims, 13 pgs.

\* cited by examiner

REAL-TIME SAMPLING SYSTEM

RELATED APPLICATIONS

This application claims the benefit of U.S. Provisional Application Ser. No. 62/892,256, filed Aug. 27, 2019, and U.S. Provisional Application Ser. No. 62/923,262, filed Oct. 18, 2019, the contents of which are hereby incorporated by reference.

BACKGROUND

The statements in this section merely provide background information related to the present disclosure and may not constitute prior art.

The tools that are currently available for the ultrasound visualization and sampling of peripheral lung tumors are limited in their range of motion and diagnostic capabilities. Typically, during peripheral sampling a guide sheath is fed through a bronchoscope and extended so far beyond the reach of the bronchoscope that the distal end of the guide sheath is not visible. A radial endobronchial ultrasound (EBUS) miniprobe is first passed through the guide sheath and used to determine the approximate location of the tumor.

Unfortunately, a peripheral tumor that is located off to one side of an airway (as opposed to one that is centered around an airway) has a substantially lower diagnostic yield in part due to the limitations of current radial EBUS technology, which allows the operator to discern the depth from the probe, but not the direction of the tumor. A sampling needle must extend off-axis from the length of the catheter and, therefore, requires a knowledge of rotational orientation of the needle and the sampling target. The radial ultrasound probe does not show the orientation of the needle to the lesion. The radial ultrasound image is a 360° image that allows the user to see a lesion, however, the user cannot tell if the needle is pointing towards the lesion.

SUMMARY

The present invention provides a device for allowing real-time viewing of a tissue sampling or drug delivery procedure in a patient beyond the viewing range of an endoscope that may be used to transport the device.

An exemplary device includes a sheath that has at least two lumens and a handle. The handle includes a connector that connects to a proximal end of an endoscope, a shaft portion that rotatably connects to a proximal end of the connector and a manifold that is slidably received by the shaft portion. The manifold includes a distal end that connects to the sheath. The distal end includes at least two lumens, wherein each lumen has a longitudinal axis that aligns with a respective one of the at least two lumens of the connected sheath. The manifold also includes a first proximal port having a longitudinal axis that matches the longitudinal axis of one of the distal end and a second proximal port that includes a longitudinal axis that is at an angular relationship to the longitudinal axis of a second one of the two lumens of the distal end. The first proximal port receives a radial ultrasound probe and the second proximal port receives a medical tool. The second proximal port allows the medical tool to pass to the second one of the two lumens of the distal end.

In one aspect, the medical tool includes a needle. An actuator includes a distal end that connects to a proximal end of the needle and a proximal end that connects to an aspirating source.

In another aspect, the shaft portion includes a anti-buckling device that limits buckling of at least one of the sheath or the medical tool within the shaft portion and the manifold includes a anti-buckling device that limits buckling of the medical tool within the manifold. The anti-buckling device may include telescoping tubes.

In still another aspect, the sheath include a distal end having a distal support member, a proximal support member, and at least two longitudinal support members connected between the distal support member and the proximal support member. The distal support member, the proximal support member and the at least two longitudinal support members are formed from a machined, stamped or laser-cut hypotube. The distal support member and the proximal support member are ring-shaped.

In yet another aspect, the distal end includes a ramp that allows a distal end of the medical tool to deflect as the medical tool is advanced distally. The proximal support member includes a support that provides support for the ramp.

In still yet another aspect, the second proximal port receives the medical tool in a predefined orientation such that when the medical tool is received in the second proximal port, the distal end of the medical tool is at a predefined orientation relative to the ramp.

Further features, advantages, and areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way. The components in the figures are not necessarily to scale, emphasis instead being placed upon illustrating the principles of the invention. In the drawings:

FIG. 6-1 is a side view of the distal end;

FIG. 6-2 is a top view of the distal end;

FIG. 6-3 is a perspective view of a component of the distal end;

FIG. 6-4 is a top view of the component of the distal end shown in FIG. 6-3;

FIG. 8-1 shows a side view of the distal end, an ultrasound plane produced by an ultrasound transducer and a target lesion;

FIG. 8-2 shows an ultrasound image where the ultrasound transducer is in a first orientation relative to the target lesion;

FIG. 8-3 shows an ultrasound image where the ultrasound transducer is in a second orientation relative to the target lesion;

FIG. 9-1 shows a portion of a handle of the RTS;

FIG. 9-2 shows the handle portion of FIG. 9-1 in a partially exploded view;

FIG. 9-3 shows an x-ray view of a portion of the handle of the RTS;

DETAILED DESCRIPTION

The following description is merely exemplary in nature and is not intended to limit the present disclosure, application, or uses.

Figure 1:
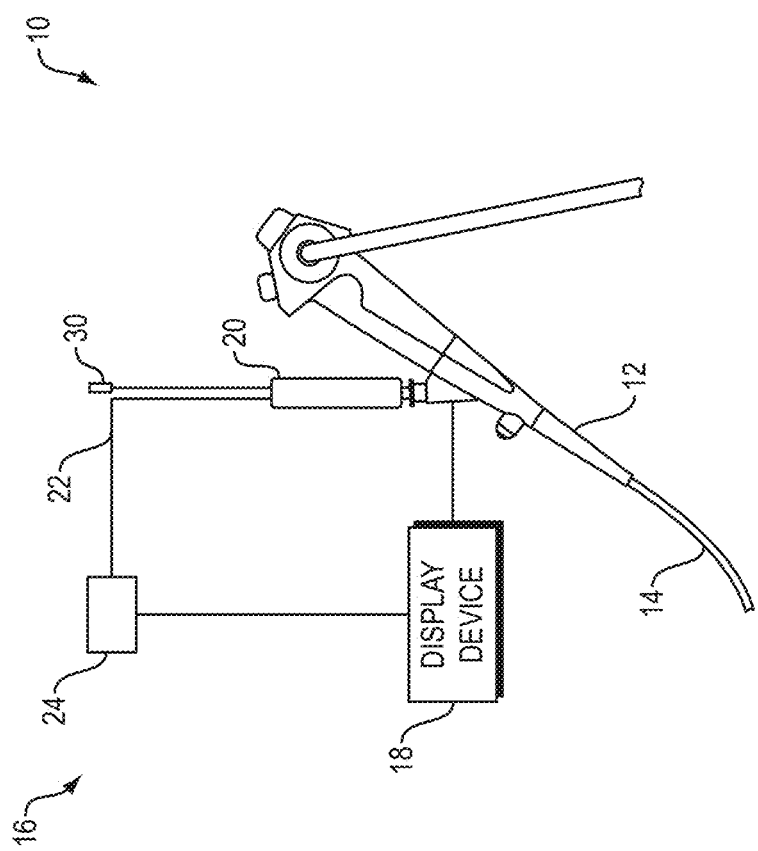
FIG. 1 shows a real-time system (RTS) and an endoscope.

Referring now to FIG. 1, a bronchoscope system 10 includes a bronchoscope 12 with an insertion tube 14, and a real-time system 16. The real-time system 16 includes a handle 20, a signal processor 24, a display device 18 and a radial ultrasound probe 22. The radial ultrasound probe 22 and a medical device 30, such as a needle for sampling and/or medicant delivery, are received within the bronchoscope 12 via the handle 20.

The display device 18 is in wired or wireless signal communication with the bronchoscope 12 and/or the signal processor 24. The display device 18 presents images generated based on information received from the bronchoscope 12 and/or the signal processor 24 that receives image information from a bronchoscope imaging device and/or a radial ultrasound transducer at the distal end of the radial ultrasound probe 22. A therapeutic bronchoscope (e.g., BF-X190 produced by Olympus®) is an example of the bronchoscope 12 and the radial endobronchial ultrasound (EBUS) miniprobes produced by Olympus® are examples of the radial ultrasound probe 22.

Figure 2:
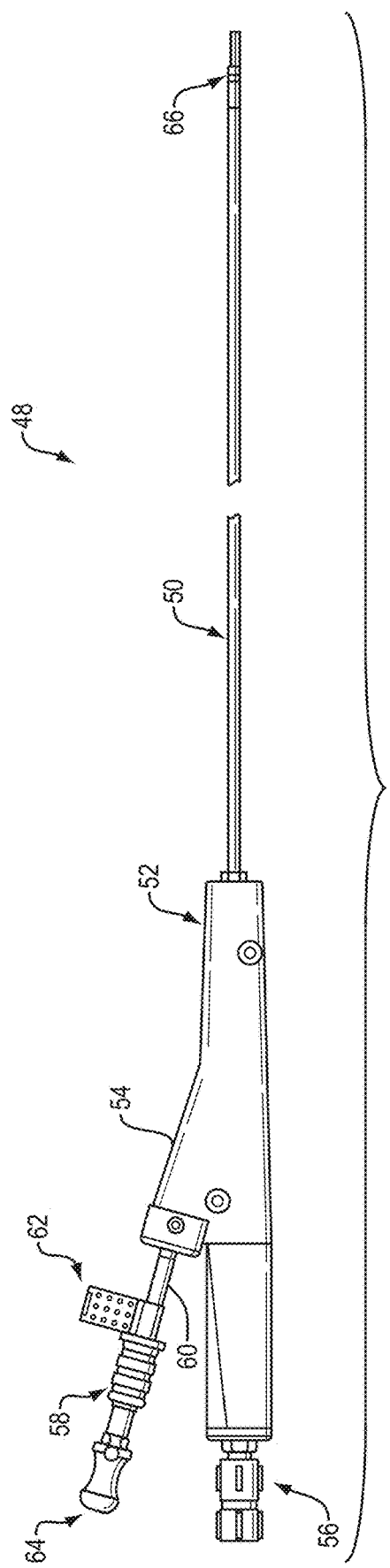
FIG. 2 shows a side view of an RTS.
Figure 3:
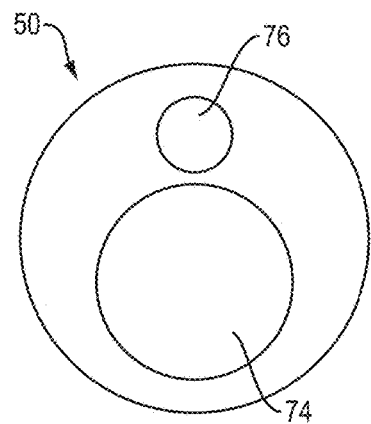
FIG. 3 is a cross-sectional view of a sheath of the RTS component shown in FIG. 2.
Figure 4:
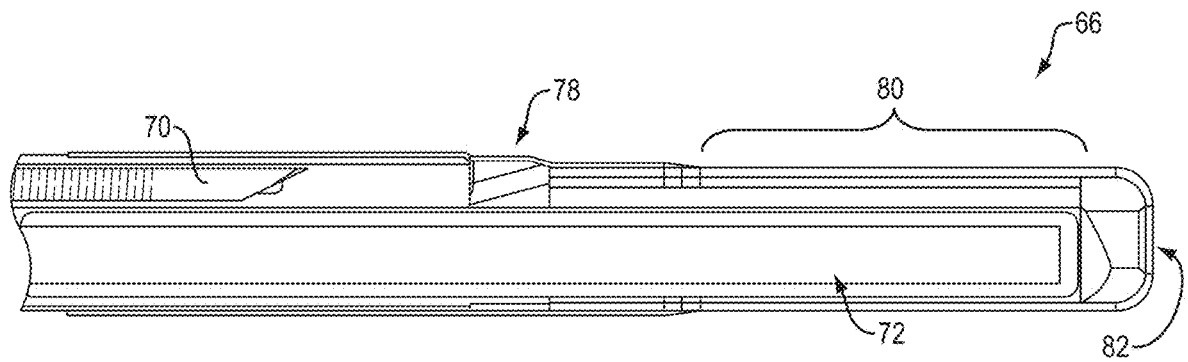
FIG. 4 is a longitudinal cross-sectional view of a distal end of the RTS shown in FIG. 2.

FIGS. 2-4 illustrate a floating real-time sampling device (RTSD) 48 having a multi-lumen sheath 50 that extends past the distal end of an endoscope (e.g. the bronchoscope 12). The endoscope is used for steering the RTSD 48 into selected airways. A handle 52 of the floating RTSD 48 does not attached to the endoscope. A flexible needle 70 is inserted into an angled side port 54 of the handle 52. A second non-angled access port 56 receives a radial EBUS probe 72. The proximal end of the needle 70 is attached to a removable needle actuator 58 that includes a distal portion 60 that is received within the angled side port 54. A safety stop component 62 attaches to the distal portion 60. The safety stop component 62 makes contact with the angled side port 54 when the needle actuator 58 is advanced distally. The safety stop component 62 is sized and/or positioned on the distal portion 60 to limit how far the distal tip of the needle 70 extends beyond the sheath 50. In one embodiment, the safety stop component 62 allows the needle 70 to extend just beyond an ultrasound plane produced by an ultrasound transducer of the radial EBUS probe 72 when the probe 72 is inserted into the sheath 50. The needle actuator 58 includes a proximal port for receiving a stylet (not shown) that attaches to a stylet knob 64 or for connecting to a syringe for creating suction pressure via a Luer or similar fitting. In one embodiment, the stylet is curved at a distal portion for causing the needle 70 to conform to the curve once both have exited the sheath 50.

The sheath 50 includes a radial EBUS probe lumen 74 for receiving the probe 72 and a smaller working channel lumen 76 for receiving the needle 70 or another medical device. A distal tip 66 of the sheath 50 includes an exit ramp 78 for the working channel lumen 76 and a window 80 that surrounds a portion of the radial EBUS probe lumen 74. The window 80 is distal to the exit ramp 78. A port 82 at the distal end of the sheath 50 allows ultrasound gel to be inserted into the lumen 74.

FIGS. 5, 6-1, 6-2, 6-3 and 6-4 show an example of the distal tip 66 of the sheath 50. In one embodiment, the distal tip 66 is formed from a hypotube 88 that has been processed (machined, stamped or etched) to include a distal ring 90, a proximal ring 92 and two orientation pins (i.e., longitudinal components, ultrasound reflective or echogenic members) 94 that extend between the rings 90, 92. A casing material, such as Pebax® or comparable material, is applied (molded or reflowed) over the hypotube and over a section of the catheter adjacent to the hypotube using a mandrel or comparable tooling.

In one embodiment, the hypotube 88 is pressed into a plastic mold or overmolded and is aligned to the probe lumen 74 of the sheath 50 using a mandrel.

Figure 7:
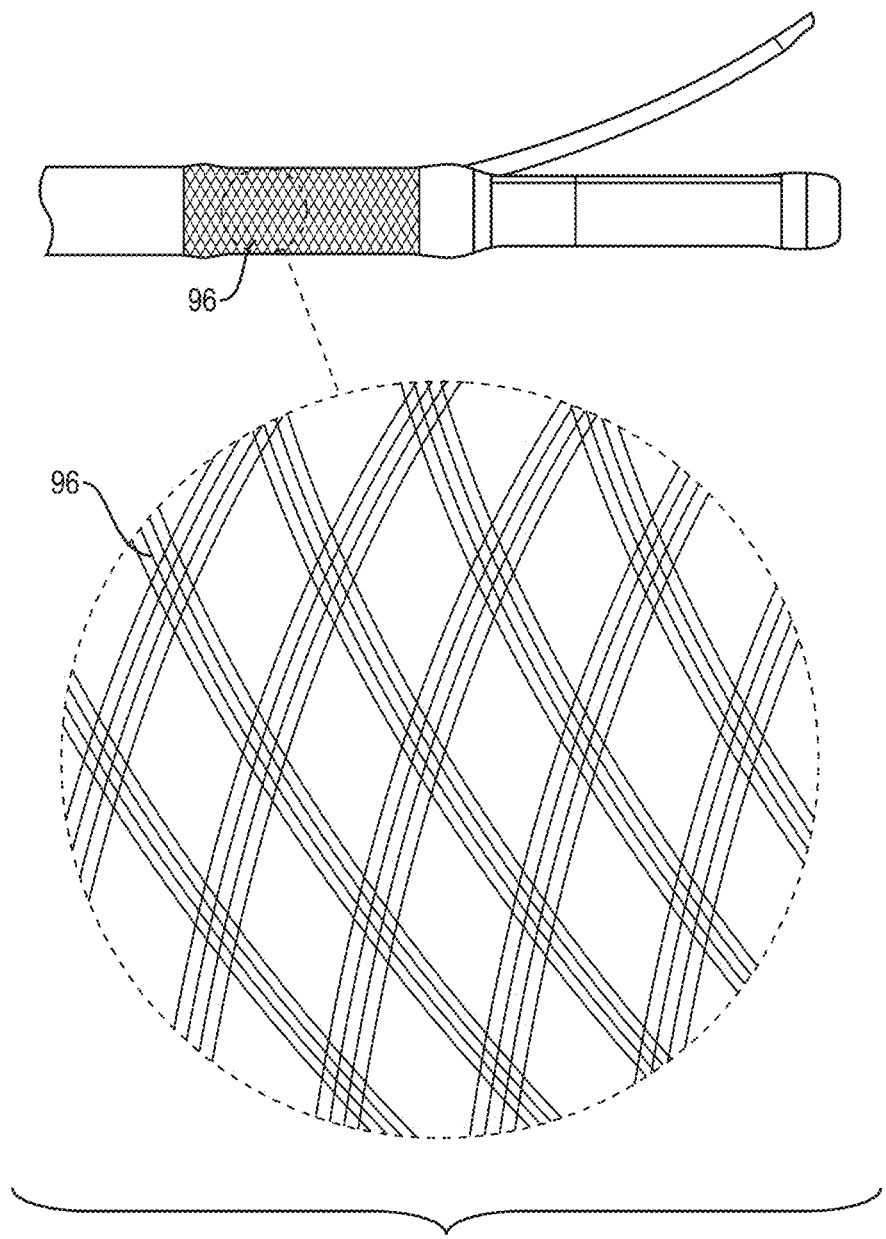
FIG. 7 is an expanded view of a braided section of the distal end.

As shown in FIG. 7, a section of the sheath 50 just proximal to the distal tip 66 may include a braided section 96 of thin wires (e.g., stainless steel) that surround the radial EBUS probe lumen 74 and the working channel lumen 76. The braided section 96 provides increased torque response and a tighter bend radius without sacrificing too much flexibility. The braided section 96 may also reduce the risk of a tool (e.g., needle) from penetrating the lumen and sheath walls. In one example, the braided section 96 includes a spiral of three adjacent wires.

Figures 1, 8:
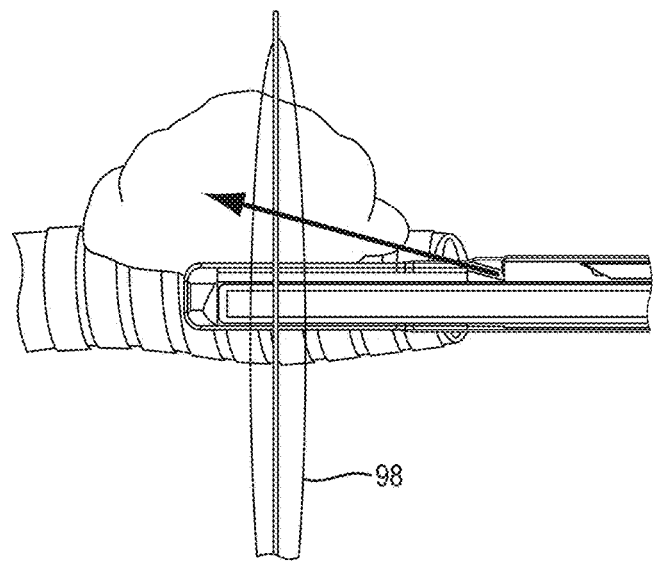
Figures 2, 8:
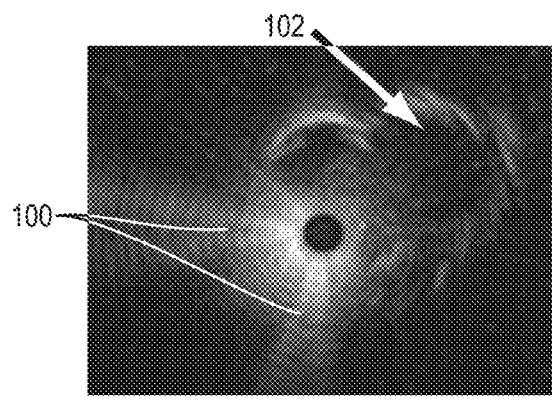
Figures 3, 8:
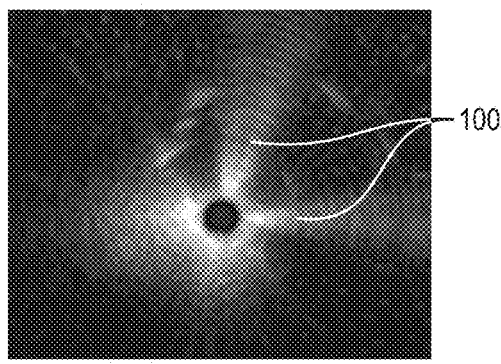
Figures 3, 9:
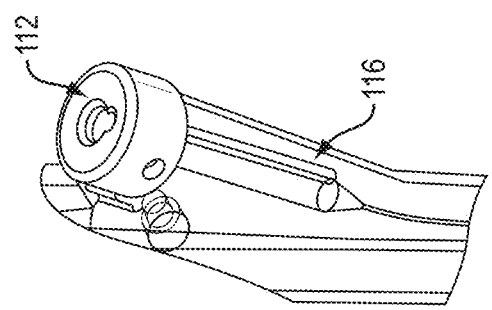
Figures 2, 9:
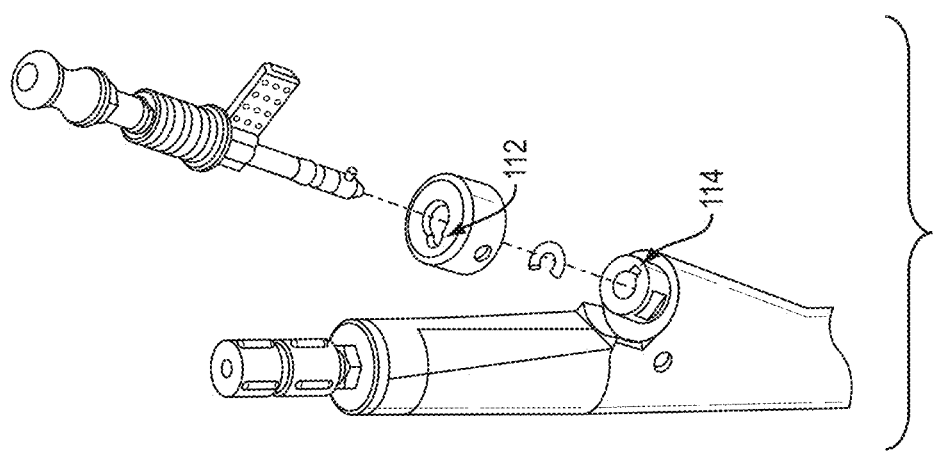
Figures 1, 9:
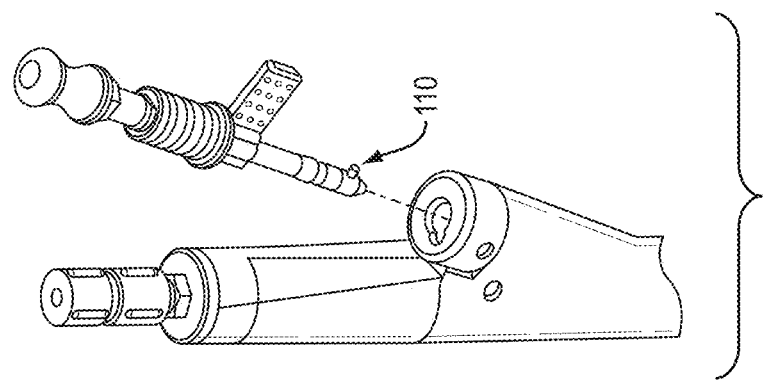
Figure 10:
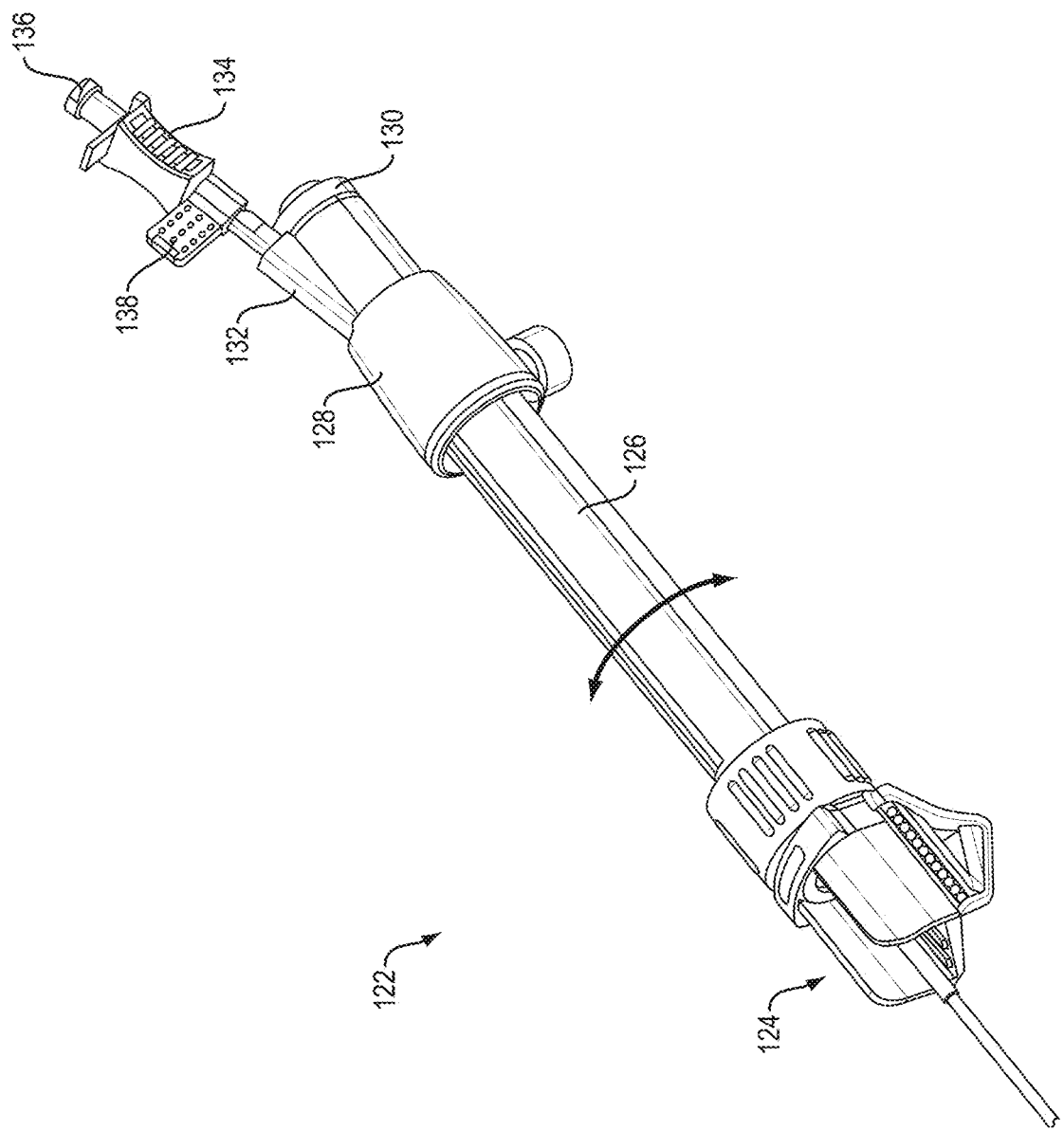
FIG. 10 is an exemplary RTS handle.
Figure 11:
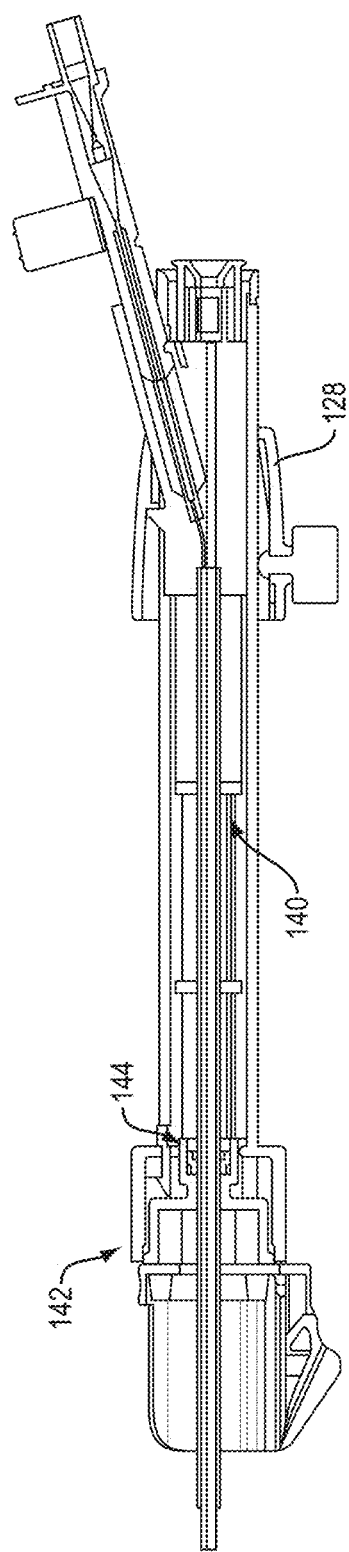
FIG. 11 is a longitudinal cross-sectional view of the handle shown in FIG. 10.
Figure 12:
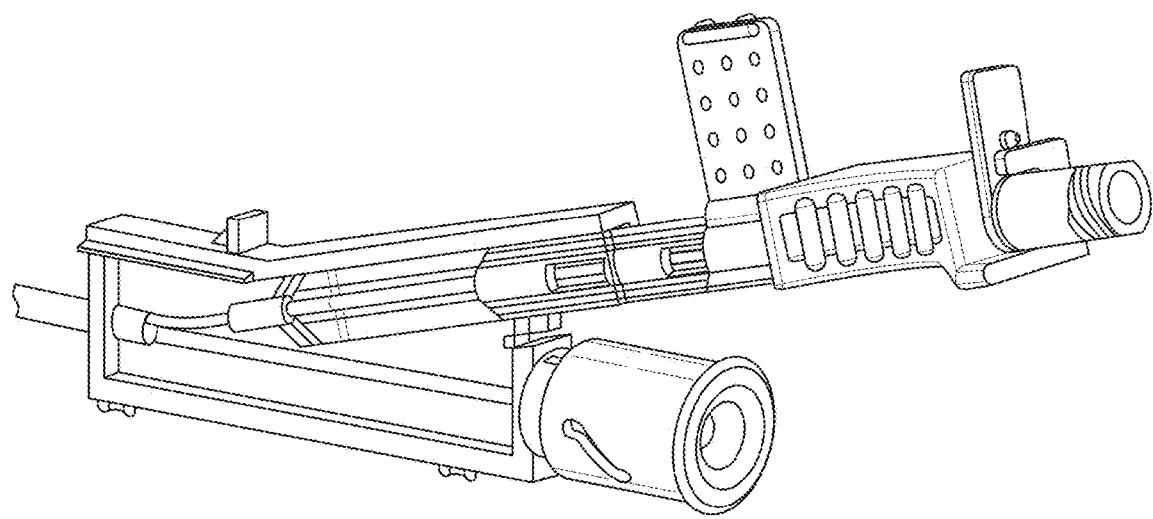
FIG. 12 is a partial cross-sectional view of a proximal end of the handle shown in FIG. 10.
Figure 13:
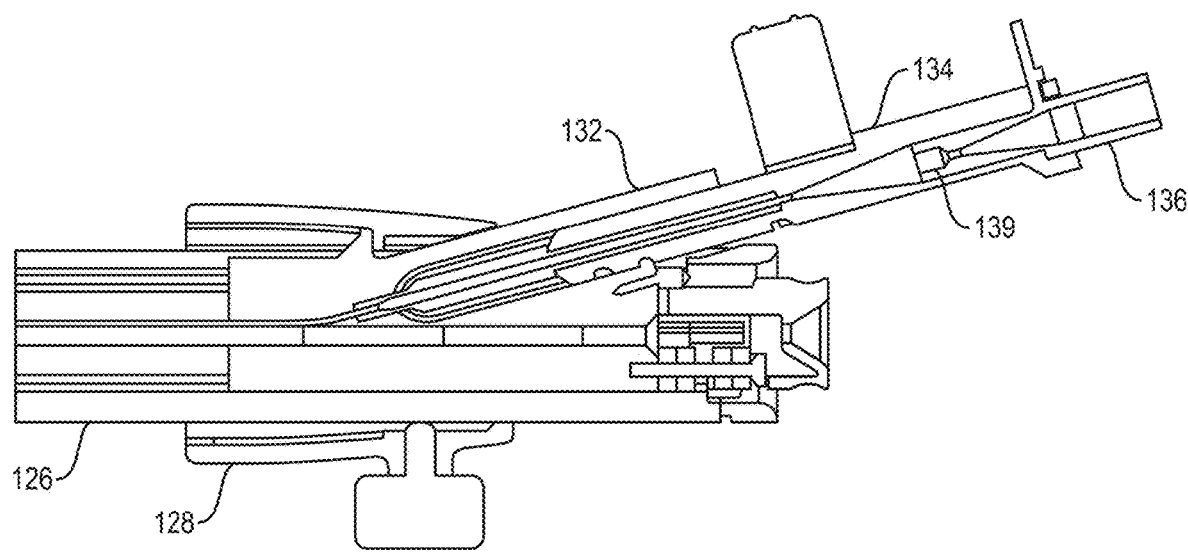
FIG. 13 is a second cross-sectional view of a proximal end of the handle shown in FIG. 10.

FIG. 8-1 shows a side view of the distal end 66 positioned adjacent to a target. The ultrasound probe 72 received within the distal end 66 produces the ultrasound images shown in FIGS. 8-2 and 8-3 based on an ultrasound plane 98 produced by the transducer of the ultrasound probe 72. The orientation pins 94 produce ultrasound artifacts that appear as headlights 100 in the ultrasound images. The headlights 100 allow an operator to understand orientation of the distal end 66 relative to a target. With a knowledge of orientation, the operator can rotate the sheath 50 using the handle so that a target tumor (see reflection 102) is at a proper position relative to where the needle 70 will exit the sheath 50.

FIGS. 9-1, 9-2 and 9-3 show a keying mechanism for the needle 70 and the needle actuator 58 to be properly keyed relative to the sheath 50. The distal portion 60 of the needle actuator 58 includes an actuator keying pin 110 at its distal end. An angled side port 54 of the handle 52 includes two offset keyways 112, 114. One keyway 114 is built into the port 54. The other keyway 112 is a separate piece that rotates over the built-in keyway 114. The keyways 112, 114 are intentionally misaligned so that the user must rotate the actuator 58 in order to remove it from the handle 52. To insert the actuator: 1) Align the keying pin 110 with the first keyway 112; 2) Push beyond a segmented O-ring; 3) Then rotate counter-clockwise to align with second keyway 114 to insert the remainder of the actuator 58. The actuator 58 will click into the O-ring when it is fully inserted.

In one embodiment, FIGS. 10-13 show an exemplary RTS handle 122 that includes a scope attachment portion 124, a handle shaft 126, and a manifold 128. The scope attachment portion 124 attaches to a port of an endoscope handle. The handle shaft 126 attaches to the scope attachment portion 124 such that the handle shaft 126 can rotate about a longitudinal axis. The handle shaft 126 slidably receives the manifold 128. The manifold 128 is attached to a multi-lumen sheath (e.g., the sheath 50) that is received within an attached scope. The manifold 128 includes a first port 130 that receives an ultrasound probe (e.g., the probe 72) and a second angled port 132 that receives an actuator handle 134 that provide control of a medical device (e.g., the needle 70, cytology brushes, forceps, etc.). The first port 130 may include a low force retention device. The low force retention device keeps the probe 72 from moving longitudinally relative to the handle 122 without crushing a sheath of the probe 72.

The handle 134 includes a proximal port that receives a luer fitting 136. The luer fitting 136 includes a medical device attachment point 139 that gets bonded to the proximal end of a medical device (not shown). The luer fitting 136 receives a stylet (not shown) through a proximal port and guides the stylet into the hollow medical device via a tapered lumen. The luer fitting 136 includes a tab that when it engages with the actuator handle 134 in order to clock the distal end of the medical device to be properly oriented with regard to the ramp at the distal end of the catheter. The luer fitting 136 and attached medical device (e.g., needle) can be removed from the actuator handle 134 after a tissue sample has been acquired without having to remove the actuator handle 134 from the manifold 128 and the handle 122.

The actuator handle 134 includes a plunger and a sliding upper hypotube. The plunger and sliding upper hypotube always remain attached within the actuator handle 134. The manifold 128 includes a stationary lower hypotube. The sliding upper hypotube is sized to be received within the stationary lower hypotube. These telescoping hypotube reduce needle buckling within the handle 122.

The handle shaft 126 includes one or more internal plates 140 that provide lateral support to the received sheath and/or needle to keep them from buckling. The plates 140 slide next to each other and so they can nest very closely along the axial dimension as the manifold 128 moves distally. The manifold 128 attaches to an adjacent one of the plates 140 so that it can pull the plates 140 apart or push them together as the sheath is retracted or extended. The plates 140 are interlocking when they are extended and are kept in place using a rail system that is designed into the handle shaft 126. An O-ring 144 is located between the handle shaft 126 and the scope attachment portion 124 in order to maintain vacuum capabilities within the handle 122. The handle shaft 126 connects to the scope attachment portion 124 with a rotary detent 142.

In one embodiment, the stylet is pre-curved at the distal end. The curved stylet causes the needle to curve when outside of the sheath.

Figure 14:
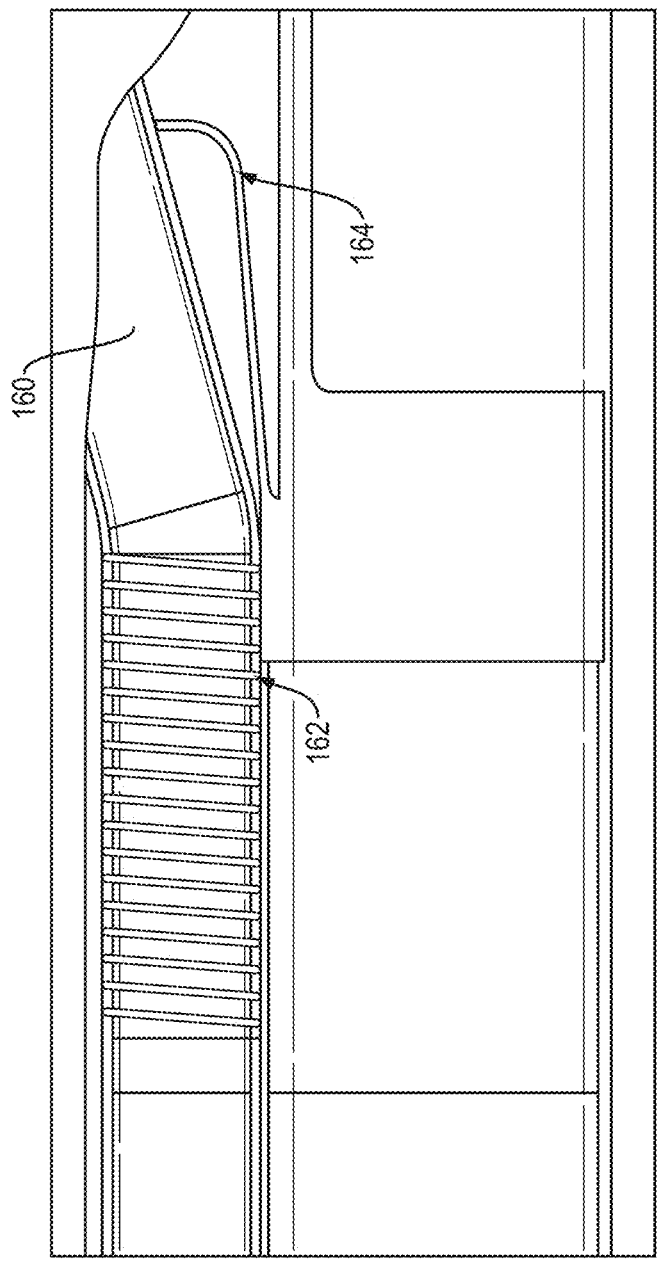
FIG. 14 is a cross-sectional view of a portion of the distal end of the RTS.

The component in the handle 122 clocks the bevel of the needle to the handle 122 for proper alignment of a needle to a distal exit ramp (FIG. 14). The handle 122 also includes a removable stop 138. The position of the stop 138 on the handle 134 signifies where the needle crosses the ultrasound plane produced by the ultrasound probe.

The manifold 128 includes a telescoping tube to reduce needle buckling.

As shown in FIG. 14, an exit ramp of the second lumen of the catheter may be made of a hard plastic (e.g., polyimide, PEEK), nitinol or stainless steel or other comparable materials. The exit ramp may be formed from a single tube with a straight proximal end 162 and a distal section 160.

Figure 5:
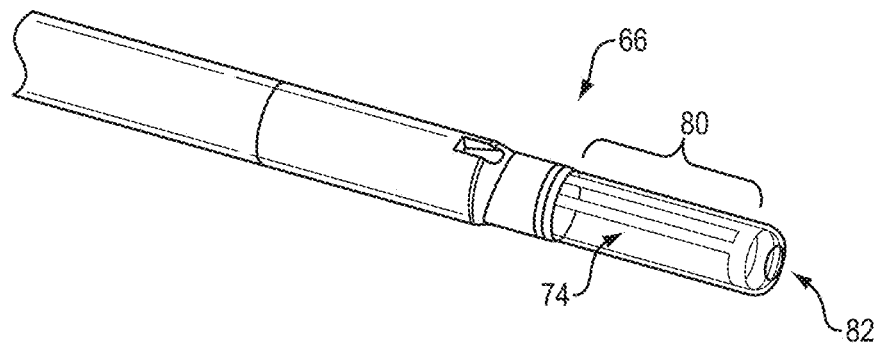
FIG. 5 is a perspective view of the distal end.
Figures 1, 6:
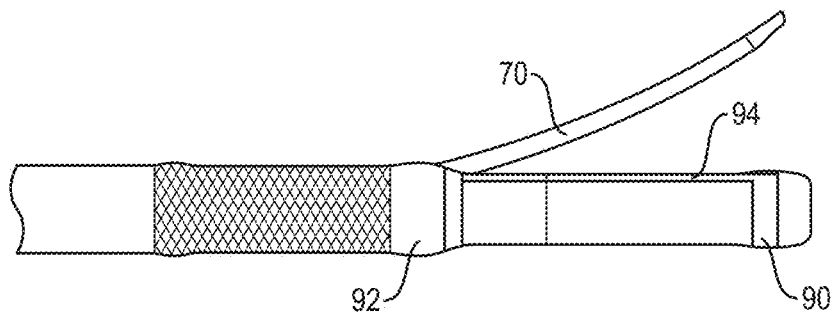
Figures 2, 6:
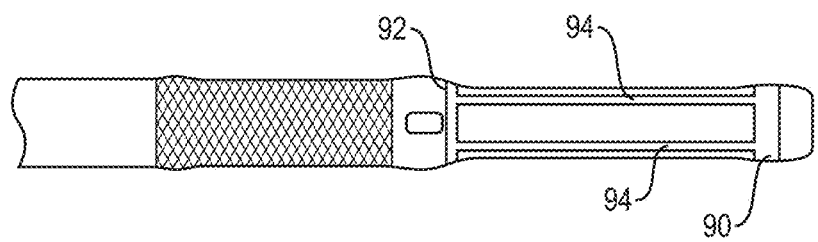
Figures 3, 6:
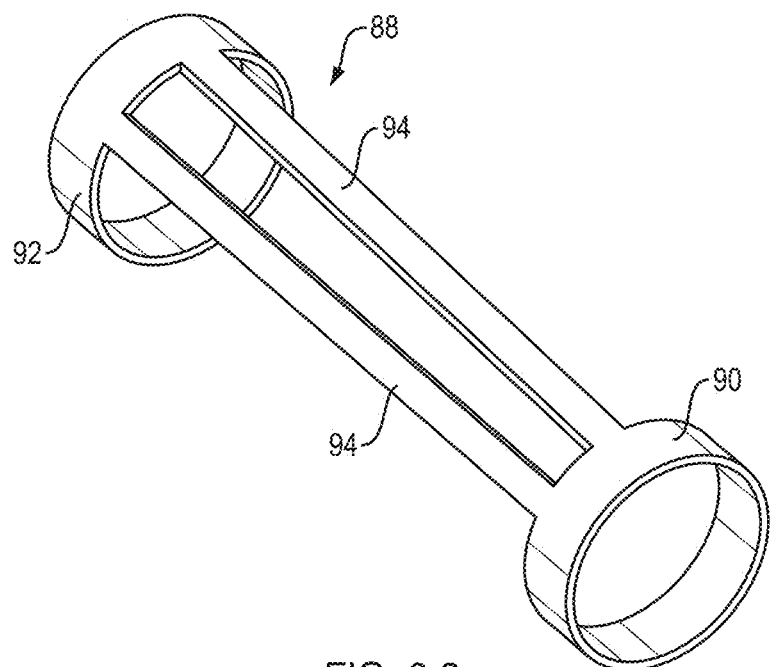
Figures 4, 6:
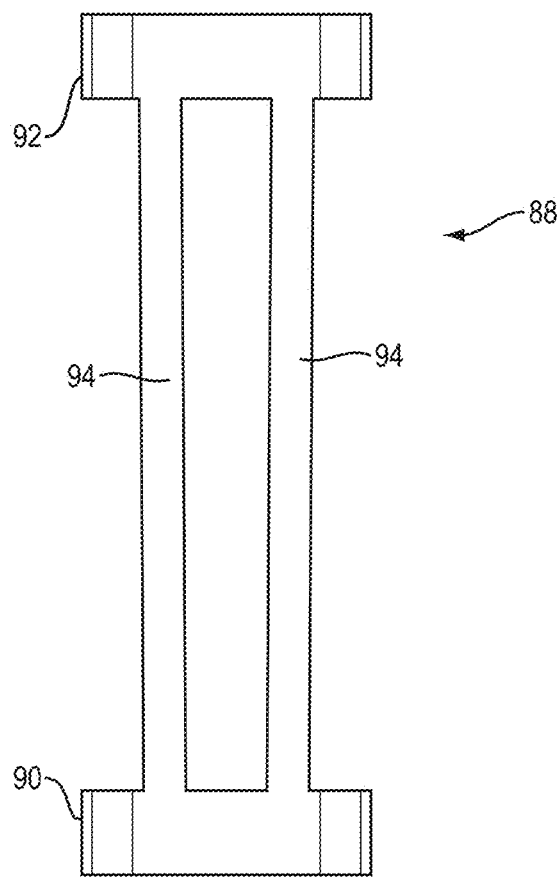

In one embodiment, the ramp distal section 160 is supported by a piece 164 of a hypotube similar to that shown in FIGS. 5, 6-1 thru and 6-4. The piece 164 is curved or bend such that a portion (e.g., distal end) provide support for the ramp distal section 160. In one embodiment, the piece 164 is formed to become the interior surface for the ramp distal section 160.

Figure 15:
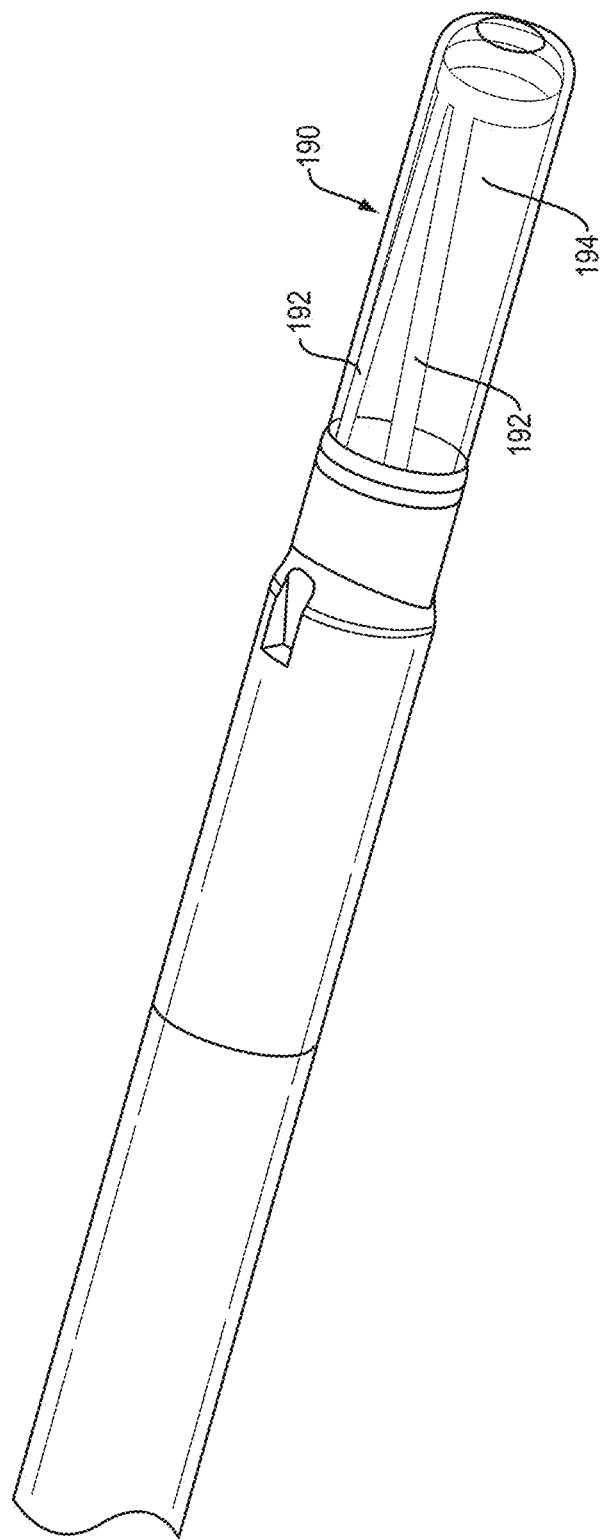
FIG. 15 is a perspective view of a distal end of an RTS.

As shown in FIG. 15, an exemplary distal end 190 includes headlight pins 192 that are at an angle relative to a longitudinal axis of a probe lumen 194. When an ultrasound transducer (i.e., the ultrasound plane) moves distally, a visual difference will be noticed in the produced image. The ultrasound artifacts produced by the pins 192 will move in the appear to converge in the produced image as the probe is advanced. This could help a user define where the needle will come out. Also, it would help a user to know where the probe is located within the tip.

Figure 16:
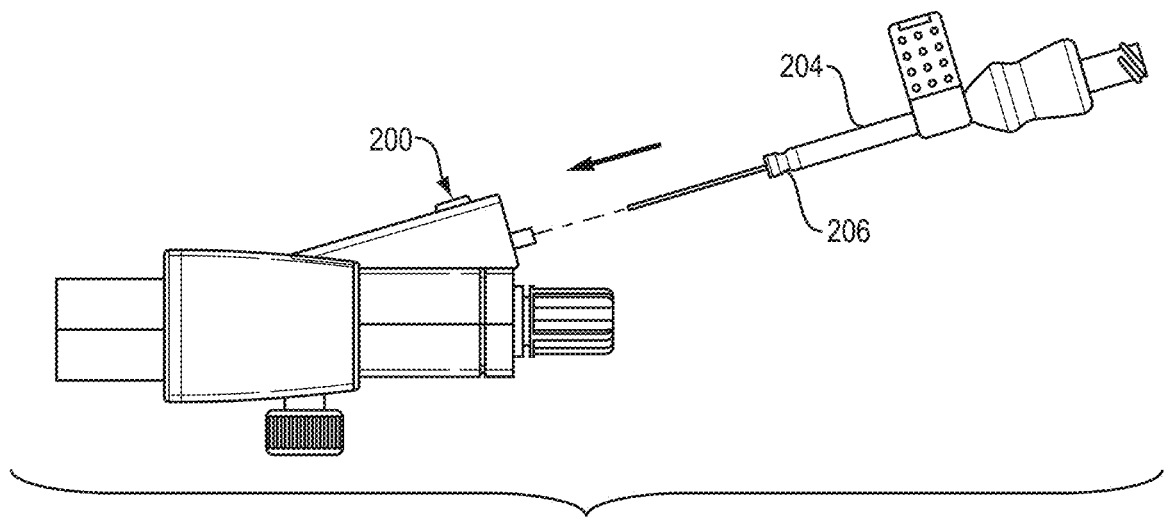
FIG. 16 is a side view of a proximal end of an exemplary RTS handle.
Figure 17:
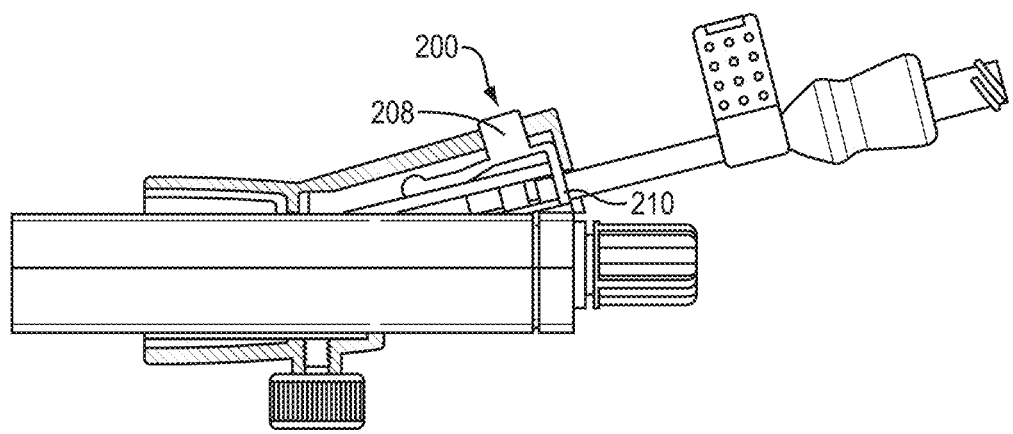
FIG. 17 is a side, partial x-ray view of the RTS handle shown in FIG. 16.

As shown in FIGS. 16 and 17, a needle handle shaft 204 includes a full or partial annular groove 206 at or near the distal end. The second angled port of the manifold includes a safety device 200 that prevents incidental needle advancement beyond the end of the needle sheath. The safety device 200 includes a button 208 attached to a spring-loaded actuator arm that is secured distally within the angled port. A proximal end of the actuator arm includes a circular or semi-circular shaped device that is positioned around the lumen defined by the angled port.

In one embodiment, the groove 206 is defined by a tapered edge on a proximal side and a perpendicular edge on the distal side. Upon advancement of the needle handle shaft 204 into the manifold, the circular or semi-circular shaped device of the safety device 200 engages with the groove 206 with a snapping or clicking action and/or sound. The distal advancement of the needle handle shaft 204 continues once the force applied to the needle handle shaft 204 exceeds a threshold amount, thus forcing the circular or semi-circular shaped device to deflect via the tapered edge. The distal advancement of the needle handle shaft 204 may also continue after depressing the button 208 to disengage with the needle handle shaft 204.

As the needle handle is retracted after the needle has been deployed or the groove 206 is distal of the circular or semi-circular shaped device, the circular or semi-circular shaped device is received into the groove 206. Because of the perpendicular edge of the groove 206, proximal motion of the needle handle shaft 204 is arrested. In order to continue retraction past this arrested position, the user depresses the button 208 thereby moving the circular or semi-circular shaped device so that it no longer is blocking the perpendicular edge of the groove 206.

Embodiments

A. A device comprising: a sheath comprising at least two lumens; and a handle comprising: a connector configured to connect to a proximal end of an endoscope; a shaft portion configured to be rotatably connected to a proximal end of the connector; and a manifold configured to be slidably received by the shaft portion, the manifold comprising: a distal end configured to connect to the sheath, the distal end comprising two lumens each having a lumen with longitudinal axis that are aligned with respective ones of the at least two lumens of the connected sheath; a first proximal port having a longitudinal axis configured to match the longitudinal axis of one of the tow lumens of the distal end, wherein the first proximal port is configured to receive a radial ultrasound probe; and a second proximal port configured to receive a medical tool, the second proximal port comprises a longitudinal axis that is at an angular relationship to the longitudinal axis of a second one of the two lumens of the distal end, wherein the second proximal port is configured to allow the medical tool to pass to the second one of the two lumens of the distal end.

B. The device of A, wherein the shaft portion includes a longitudinal slot configured to slidably receive the manifold.

C. The device of A or B, wherein the medical tool comprises a needle.

D. The device of C, further comprising an actuator comprising: a distal end configured to connect to a proximal end of the needle; and a proximal end configured to connect to an aspirating source.

E. The device of any of A-D, wherein the shaft portion comprises a first anti-buckling device configured to limit buckling of at least one of the sheath or the medical tool within the shaft portion.

F. The device of any of A-E, wherein the manifold comprises a first anti-buckling device configured to limit buckling of the medical tool within the manifold.

G. The device of E or F, wherein the anti-buckling device comprises a telescoping tube.

H. The device of any of A-G, wherein the sheath comprises a distal end having a distal component, a proximal component, and at least two longitudinal components connected between the distal component and the proximal component.

I. The device of H, wherein the distal component, the proximal component and the at least two longitudinal components are formed from at least one of a machined, stamped or laser cut hypotube.

J. The device of H or I, wherein the distal support member and the proximal support member are at least partial rings.

K. The device of any of H-J, wherein the distal end comprises a ramp that allows a distal end of the medical tool to deflect as the medical tool is advanced distally.

L. The device of K, wherein the proximal support member comprises a support configured to provide support for the ramp.

M. The device of K or L, wherein the second proximal port receives the medical tool in a predefined orientation such that when the medical tool is received in the second proximal port, the distal end of the medical tool is at a predefined orientation relative to the ramp.

The description of the invention is merely exemplary in nature and variations that do not depart from the gist of the invention are intended to be within the scope of the invention. Such variations are not to be regarded as a departure from the spirit and scope of the invention.

What is claimed is:
1. A device comprising:
a sheath comprising at least two lumens;
an actuator comprising a needle handle shaft including a distal end couplable to a proximal end of a needle and a proximal end configured to connect to an aspirating source, the needle handle shaft including an annular groove adjacent the distal end; and
a handle comprising:
a connector configured to connect to a proximal end of an endoscope;
a shaft portion configured to be rotatably connected to a proximal end of the connector; and
a manifold configured to be slidably received by the shaft portion, the manifold comprising:
a distal end configured to connect to the sheath, the distal end comprising at least two lumens, wherein each lumen of the distal end has a longitudinal axis that aligns with a respective one of the at least two lumens of the connected sheath;
a first proximal port having a longitudinal axis configured to match the longitudinal axis of one of the at least two lumens of the distal end, wherein the first proximal port is configured to receive a radial ultrasound probe; and
a second proximal port configured to receive the needle, the second proximal port comprises a longitudinal axis that is at an angular relationship to the longitudinal axis of a second one of the at least two lumens of the distal end, wherein the second proximal port is configured to allow the needle to pass to the second one of the at least two lumens of the distal end; and
a lock mechanism configured to arrest distal motion of the needle handle shaft below a predefined threshold value and release the needle handle shaft upon application of a longitudinal force above the predefined threshold value, the lock mechanism including an actuator arm and a button to disengage the lock mechanism, the actuator arm configured to engage the annular groove to arrest distal motion of the needle handle shaft.

2. The device of claim 1, wherein the shaft portion includes a longitudinal slot configured to slidably receive the manifold.

3. The device of claim 1, wherein the shaft portion comprises a first anti-buckling device configured to limit buckling of at least one of the sheath or the needle within the shaft portion.

4. The device of claim 1, wherein the manifold comprises a first anti-buckling device configured to limit buckling of the needle within the manifold.

5. The device of claim 4, wherein the first anti-buckling device comprises a telescoping tube.

6. The device of claim 1, wherein the sheath comprises:
a distal end comprising:
a distal component;
a proximal component; and
at least two longitudinal components connected between the distal component and the proximal component.

7. The device of claim 6, wherein the distal component, the proximal component and the at least two longitudinal components are formed from at least one of a machined, a stamped or a laser cut hypotube.

8. The device of claim 6, wherein the distal component and the proximal component are at least partial rings.

9. The device of claim 6, wherein the distal end of the sheath comprises a ramp configured to allow a distal end of the needle to deflect as the needle is advanced distally.

10. The device of claim 9, wherein the proximal component comprises a support configured to at least provide support for the ramp or act as the ramp.

11. The device of claim 9, wherein the second proximal port is configured to receive the needle in a predefined orientation such that when the needle is received in the second proximal port, the distal end of the needle is at a predefined orientation relative to the ramp.

12. A system comprising:
an endoscope; and
a device comprising:
a sheath comprising at least two lumens;
an actuator comprising a needle handle shaft including a distal end couplable to a proximal end of a needle and a proximal end configured to connect to an aspirating source, the needle handle shaft including an annular groove adjacent the distal end; and
a handle comprising:
a connector configured to connect to a port of the endoscope;

a shaft portion configured to be rotatably connected to a proximal end of the connector; and a manifold configured to be slidably received by the shaft portion, the manifold comprising:

a distal end configured to connect to the sheath, the distal end comprising at least two lumens, wherein each lumen of the distal end has a longitudinal axis that aligns with a respective one of the at least two lumens of the connected sheath;

a first proximal port having a longitudinal axis configured to match the longitudinal axis of one of the at least two lumens of the distal end, wherein the first proximal port in configured to receive a radial ultrasound probe;

a second proximal port configured to receive the needle, the second proximal port comprises a longitudinal axis that is at an angular relationship to the longitudinal axis of a second one of the two lumens of the distal end, wherein the second proximal port is configured to allow the needle to pass to the second one of the two lumens of the distal end; and a locking device configured to arrest distal motion of the needle below a predefined force threshold value and to continue distal motion of the needle with application of a force above the predefined force threshold value, the locking device including an actuator arm and a button to disengage the locking device, the actuator arm configured to engage the annular groove to arrest distal motion of the needle.

13. The system of claim 12, wherein the shaft portion comprises an anti-buckling device configured to limit buckling of at least one of the sheath or the needle within the shaft portion and the manifold comprises an anti-buckling device configured to limit buckling of the needle within the manifold.

14. The system of claim 12, wherein the sheath comprises:
a distal end comprising:
a distal member;
a proximal member; and
at least two longitudinal members connected between the distal member and the proximal member.

15. The system of claim 14, wherein the distal end of the sheath comprises a ramp configured to allow a distal end of the needle to deflect as the needle is advanced distally.

16. The system of claim 15, wherein the proximal member comprises a support configured to provide support for the ramp.

17. The system of claim 15, wherein the second proximal port is configured to receive the actuator in a predefined orientation such that when the needle is received in the second proximal port, a distal end of the needle is at a predefined orientation relative to the ramp.

* * * * *